US008182438B2

(12) United States Patent
Rumsey

(10) Patent No.: US 8,182,438 B2
(45) Date of Patent: May 22, 2012

(54) ORTHOTIC DEVICE

(75) Inventor: Royce Rumsey, Laguna Beach, CA (US)

(73) Assignee: Bio Cybernetics International, Inc., La Verne, CA (US)

( * ) Notice: Subject to any disclaimer, the term of this patent is extended or adjusted under 35 U.S.C. 154(b) by 504 days.

(21) Appl. No.: 12/181,034

(22) Filed: Jul. 28, 2008

(65) Prior Publication Data

US 2009/0082707 A1  Mar. 26, 2009

Related U.S. Application Data

(60) Provisional application No. 60/952,422, filed on Jul. 27, 2007.

(51) Int. Cl.
*A61F 5/00* (2006.01)

(52) U.S. Cl. ........................................................ 602/19

(58) Field of Classification Search .................... 602/12, 602/14, 19; 128/96.1, 99.1, 101.1, 102.1; 2/311, 312
See application file for complete search history.

(56) References Cited

U.S. PATENT DOCUMENTS

| | | | |
|---|---|---|---|
| 4,688,558 A | 8/1987 | Hooper, Jr. et al. | |
| 5,101,811 A * | 4/1992 | Brunswick | 297/284.4 |
| 5,435,563 A * | 7/1995 | Salvatore | 473/215 |
| 5,451,200 A | 9/1995 | LaBella et al. | |
| 5,599,287 A | 2/1997 | Beczak, Sr. et al. | |
| 5,634,891 A | 6/1997 | Beczak, Sr. et al. | |
| 6,500,137 B1 | 12/2002 | Molino et al. | |
| 6,517,502 B2 | 2/2003 | Heyman et al. | |
| 6,932,780 B2 | 8/2003 | Kozersky | |
| 6,702,770 B2 | 3/2004 | Bremer et al. | |
| D518,895 S * | 4/2006 | Weaver et al. | D24/190 |
| 7,101,348 B2 * | 9/2006 | Garth et al. | 602/19 |
| 7,201,727 B2 * | 4/2007 | Schwenn et al. | 602/12 |
| 7,306,571 B2 * | 12/2007 | Schwenn et al. | 602/12 |
| 2003/0181838 A1 | 9/2003 | Garth | |
| 2006/0004313 A1 | 1/2006 | Heinz et al. | |

* cited by examiner

*Primary Examiner* — Michael Brown

(74) *Attorney, Agent, or Firm* — Sheppard, Mullin, Richter & Hampton LLP

(57) ABSTRACT

One embodiment the device described herein relates to orthotic devices, and more particularly to a modular type body brace worn about a portion of the body, and one or more removably attached body panels associated with the body brace for supporting the portion of the body. The body panels are preferably contoured to the physiology of the portion of the body and have a relatively thicker core and progressively thinner peripheral region to provide dynamic flex response when supporting the portion of the body.

25 Claims, 17 Drawing Sheets

ORTHOTIC DEVICE

RELATED APPLICATIONS

This application claims priority to U.S. provisional application No. 60/952,422 filed on Jul. 27, 2007, the contents that are incorporated by reference in their entirety.

TECHNICAL FIELD

One embodiment of the device described herein relates to orthotic devices, and more particularly to a body brace for medical and/or recuperative purposes having one or more interchangeable panels that may be adjustable, lightweight, and flexible, while having dynamic flex response in providing contoured posterior and/or anterior body comfort and support.

BACKGROUND

An orthotic device or orthosis (commonly known as a brace or splint) is an orthopedic device that is typically applied to the limb or body. Among other things, the purpose can be to provide support, protection, pain-reduction and or replacement of lost function.

In this regard, a common method of alleviating pain in people suffering from back pain, injuries and promoting healing in post-operative back surgery patients is to stabilize the spine by means of an orthosis, such as a brace. There are a large variety of braces available depending on the diagnosis and physical needs of the individual. These devices include a multitude of construction materials and designs which can be snugly fitted around the patient's trunk and peripheral area such as the cervical and pelvic regions.

Such braces are effective in achieving spinal stability if worn properly and consistently, however, most patients have difficulty in manually adjusting the brace to fit tightly enough to provide adequate support and stability. This is especially true in the case of post-operative patients who are generally in pain and frequently lack sufficient strength to make the necessary adjustments.

A custom fitted orthotic device which includes a pulley system that provides a mechanical advantage so as to require a minimal effort on the part of the patient when tightening the orthotic around the torso resulting in greater ease of donning and doffing the device, ease of adjusting the device, comfort to wearer of the device, and therefore greater patient compliance is described in U.S. Pat. No. 6,213,968, issued Apr. 10, 2001 to Heinz et al, and assigned to BioCybernetics International of Irvine, Calif., the content of which is hereby incorporated by reference in its entirety.

Although generally well suited for its intended purpose, further refinement to the Heinz et al. device, such as providing one or more interchangeable panels that may be adjustable, lightweight, flexible, and contoured, while having dynamic flex response in providing posterior and/or anterior body support will ensure still greater patient comfort, support, and resulting compliance.

SUMMARY

For the purpose of summarizing the invention certain objects and advantages have been described. It is to be understood that not all such objects or advantages may be achieved in accordance with any particular embodiment. Thus, for example, those skilled in the art will recognize that the device described herein may be embodied or carried out in a manner that achieves or optimizes one advantage or group of advantages as taught herein without necessarily achieving other objects or advantages.

One of the embodiment disclosed subject matter includes an orthotic device having a body brace worn about a portion of the body, and one or more removably attached body panels associated with the body brace for supporting the portion of the body. The body panels are preferably contoured to the physiology of the portion of the body, respond to compression of the brace, and have a relatively thicker core and progressively thinner peripheral region to provide dynamic flex response when supporting the portion of the body.

These and other embodiments will become readily apparent to those skilled in the art from the following detailed description of the preferred embodiments having reference to the attached figures, the invention not being limited to any particular preferred embodiment(s) disclosed.

DETAILED DESCRIPTION

Figure 1:
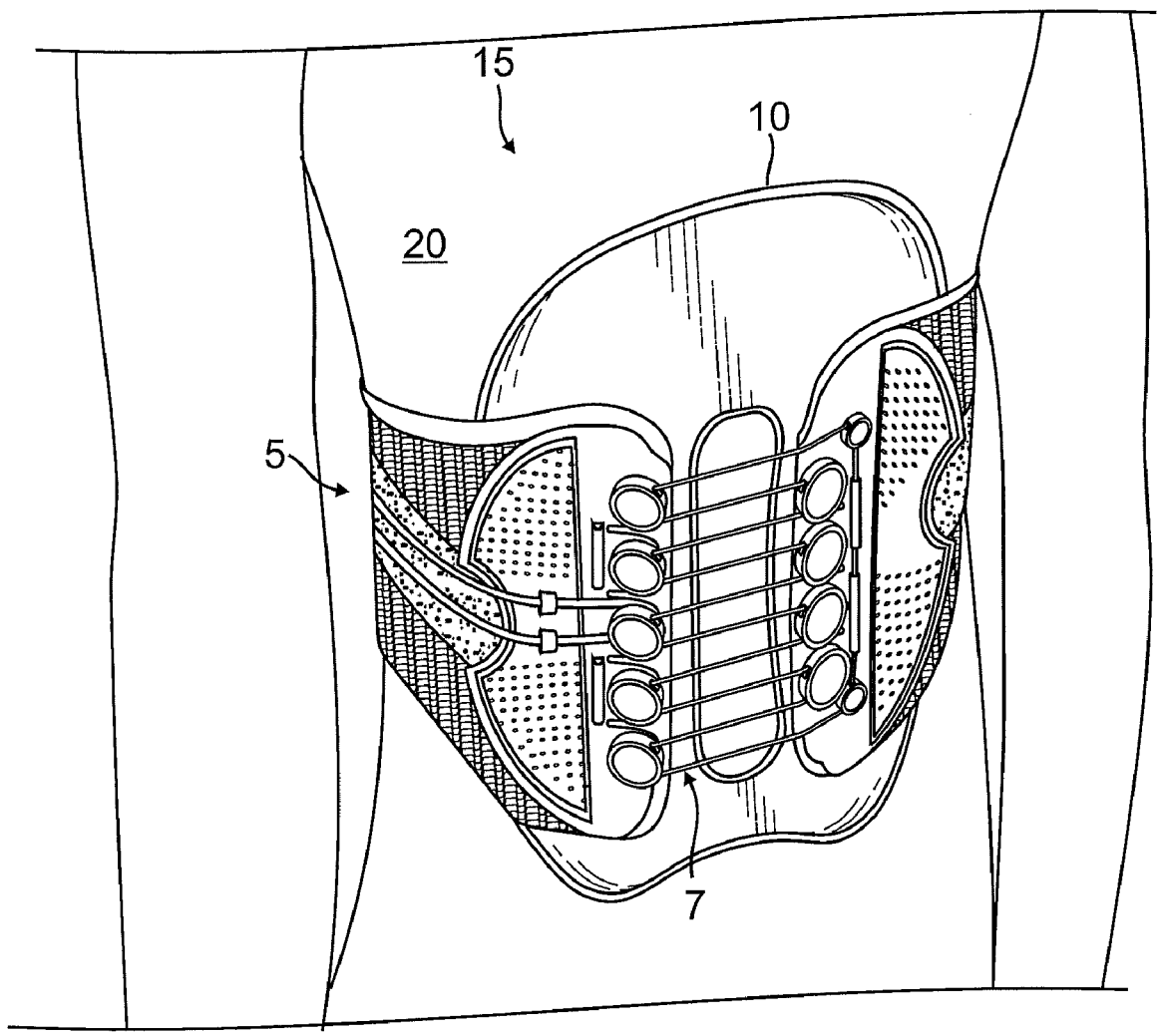
FIG. 1 shows a body brace having a mechanical advantage for tightening the brace around the torso, and a removable posterior body panel having dynamic flex response in providing patient physiology contoured compression responsive support to a posterior portion of the body.
Figure 2:
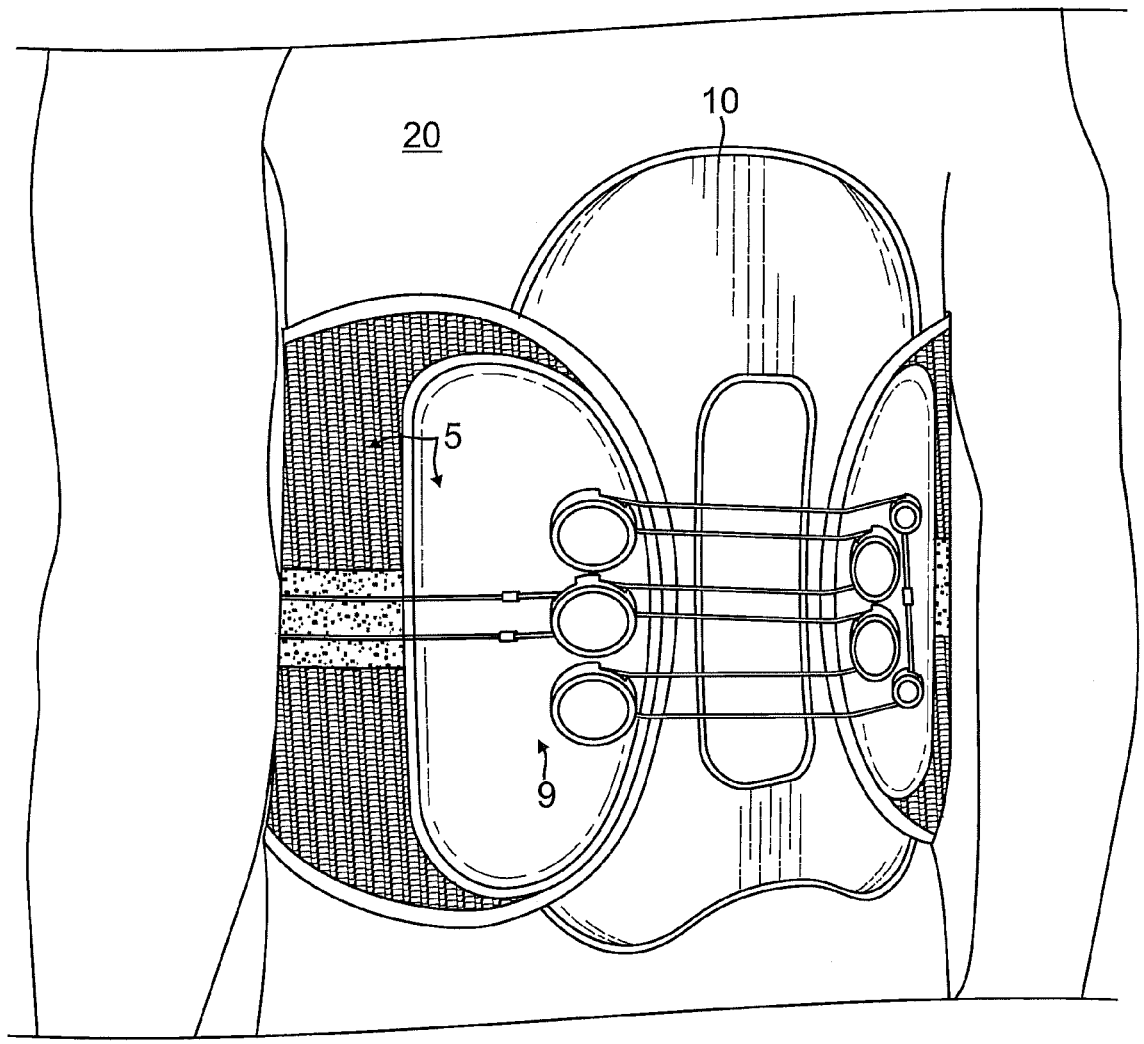
FIG. 2 shows the posterior body panel of FIG. 1 removably attached to another body brace having a mechanical advantage for tightening the brace around the torso.

Exemplary embodiments will now be described with references to the accompanying Figures, with like reference numerals referring to like elements throughout. The terminology used in the description is not intended to be interpreted in any limited or restrictive manner, simply because it is being utilized in conjunction with a detailed description of certain embodiments. Furthermore, various embodiments (whether or not specifically described herein) may include novel features, no single one of which is solely responsible for its desirable attributes or which is essential to practicing the subject matter described herein.

As shown in FIGS. 1-4, an exemplary embodiment includes an orthotic device such as the one disclosed in U.S. Pat. No. 6,213,968, issued Apr. 10, 2001, to Heinz et al. Such an orthotic device preferably includes a pulley system 7 that provides a mechanical advantage so as to require a minimal effort on the part of the patient when tightening the orthotic device around the torso. In this regard, as shown in at least FIGS. 1 and 2, the body brace 5 may assume various configurations, sizes, and shapes, however, for ease and simplicity the term "body brace" as used herein is understood to include any of the body braces shown or described herein or similar type devices not shown or described herein that provide support to the torso area in a similar manner.

The orthotic device or body brace 5 includes one or more interchangeable body panels 10 that may be adjustable, lightweight, flexible, and contoured to the physiology of the patient, while having dynamic flex response in providing anterior and/or posterior body support. As such, the ergonomic orthoses (body brace 5 and body panel 10) 15 provides for greater patient compliance by providing better device contouring, comfort, and support when compared to other devices that provide support to the torso 20.

Although other well-known methods/processes and materials may be used, preferably, all the body panels (anterior and/or posterior) described herein are constructed of polyethylene or a similar type plastic formed during an injection molding process to create a lightweight, flexible, yet sturdy and resilient body panel that is capable of providing dynamic flex response to compression or other forces when supporting anterior and/or posterior body portions. Persons of ordinary skill in the art will understand that the body panels are not limited to any particular size or dimension that may be stated herein and that the size or dimension of one or more of the body panels described herein may be adjusted or modified depending on patient body size and/or intended application.

As shown in FIG. 1, FIG. 2, FIG. 5, and FIG. 6, in one embodiment, the body brace 5 preferably includes a posterior body panel 10. The posterior body panel 10 is positioned in an area of the lower back generally over the spinal cord and is shaped to provide support to the torso 20 so as to at least minimize or prevent the spine from being hyperextended. In this regard, when properly positioned the body panel 10 extends from approximately the wearer's waist to just below the lever of the wearer's scapulas, and laterally to cover a majority of the wearer's lower back. As indicated above and shown in FIG. 5, preferably, the posterior panel 10 is contoured 25 to the physiology of the patient to contact a larger portion of the body to provide greater support and comfort than a non-contoured panel. As further indicated above, the body panel 10 is preferably lightweight and provides dynamic flex response when providing posterior body support. In this regard, the body panel 10 preferably includes a relatively stronger or more rigid core or inner portion 30 and relatively less rigid or more flexible portion at peripheral regions 35a, 35b.

Figure 5:
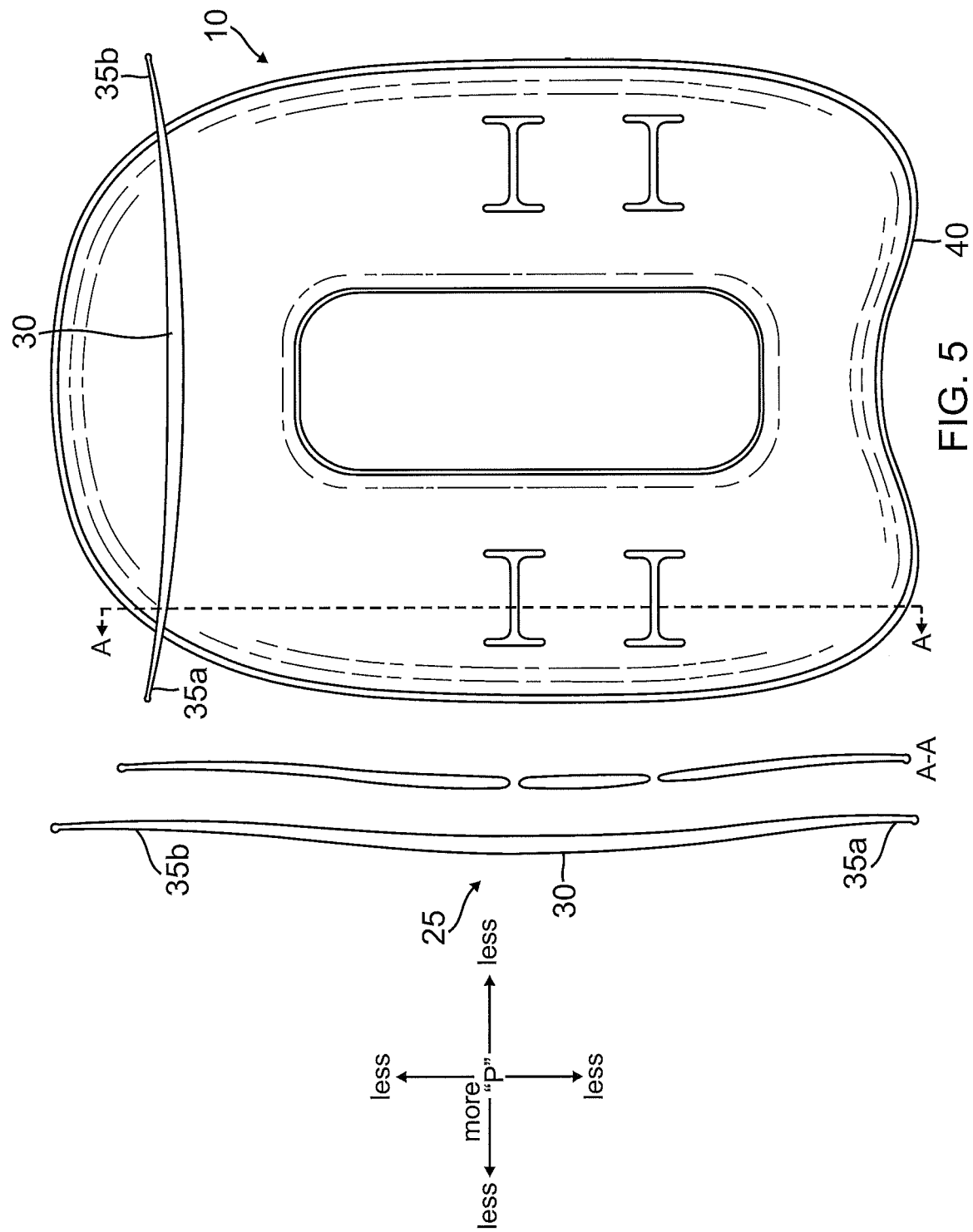
FIG. 5 shows the body panel of FIGS. 1 and 2, as well as an end view, section A-A view, and top view showing the varying thickness of the panel to facilitate progressive patient support.

As shown in the end view, top view, and cross-section A-A view of FIG. 5, the body panel 10 is relatively thicker near the center or inner portion 30 and gets progressively thinner moving toward the periphery or edges 35a, 35b of the body panel 10. In this way the body panel 10 provides a progressive support system, indicated by reference "P", i.e., relatively more support near the body's core or spine and relatively less support along the edges 35a, 35b where the body panel 10 is more forgiving to patient movement. Patient comfort may be further enhanced by a smooth bead 40 along the perimeter of the body panel 10.

Figure 6:
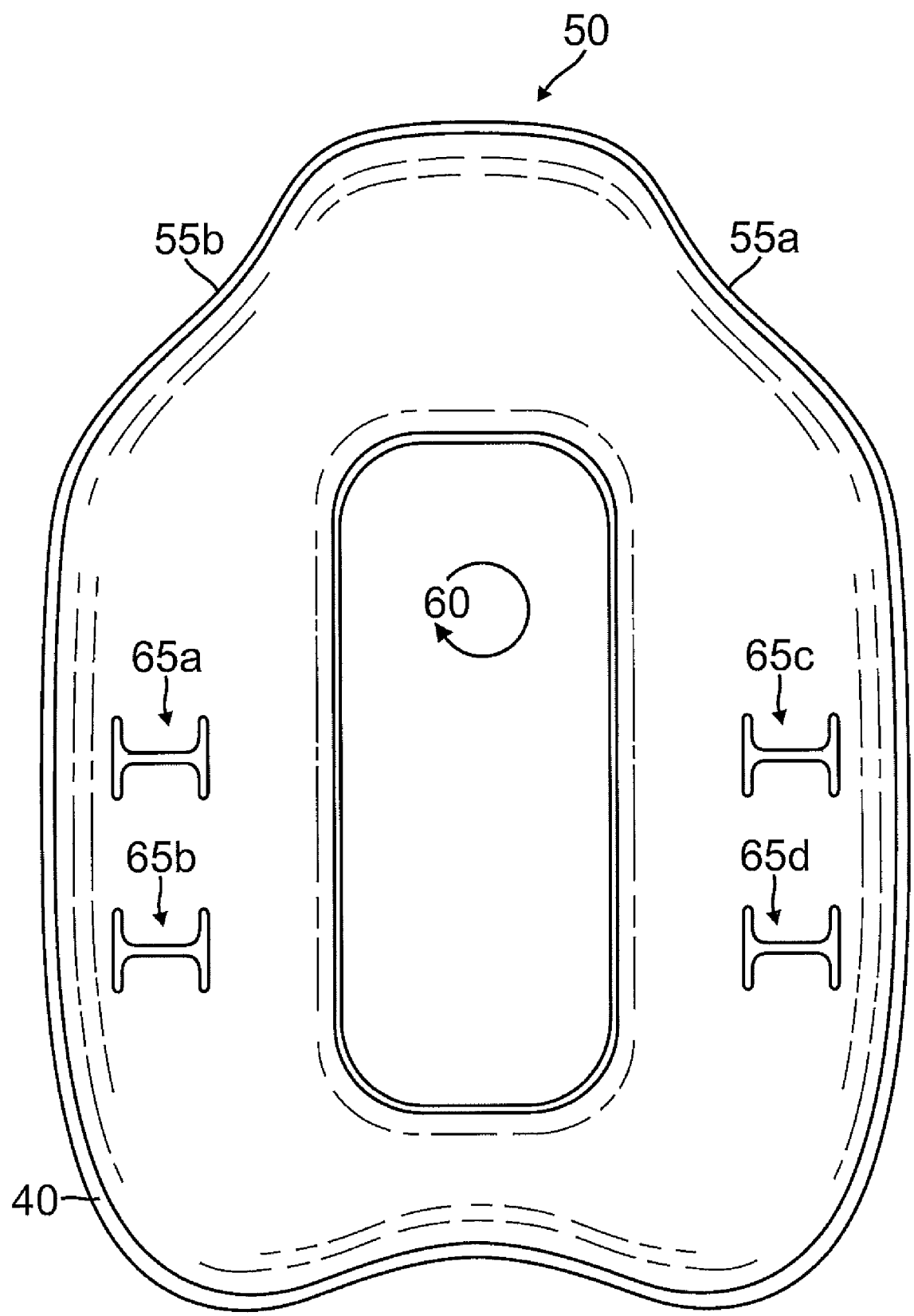
FIG. 6 shows another embodiment of a posterior body panel having dynamic flex response in providing patient physiology contoured compression support to a posterior portion of the body, the panel including, among other things, right and left relief portions shaped to allow unrestricted movement of the patient's scapula areas.

As shown in FIG. 6, the upper portion 50 of the posterior body panel 10 may include right and left relief portions 55a, 55b shaped to allow generally unrestricted movement of the patient's scapula areas. Preferably, the body panel 10 further includes a removed center section 60. Typically, this section 60 corresponds to an area of the patient's body where an incision was placed during surgery. Accordingly, the removed center section 60 may provide access to sutures, scar tissue, bandages, etc., as well as potentially promoting wound healing.

A plurality of cutouts or slots 65a-65d are provide on the posterior body panel 10 to facilitate removable attachment and vertical height adjustment of the posterior body panel 10 to the body brace 5. The cutouts 65a-65d are preferably shaped to accept a Velcro® or a similar type strap or other connecting means threaded therethrough to removably attach the posterior panel 10 to the body brace 5. By threading straps through the upper slots 65a, 65c a relatively lower vertical placement of the posterior body panel 10 on the body brace 5 and patient is achieved. Alternatively, by threading the straps through the lower slots 65b, 65d a relatively higher vertical placement of the posterior body panel 10 on the body brace 5 and patient is achieved. The geometrical design, placement, and method of attaching the straps through the slots 65a-65d allow for symmetrical compression-travel (tightening) and resulting symmetrical support of the patient's body.

Figure 3:
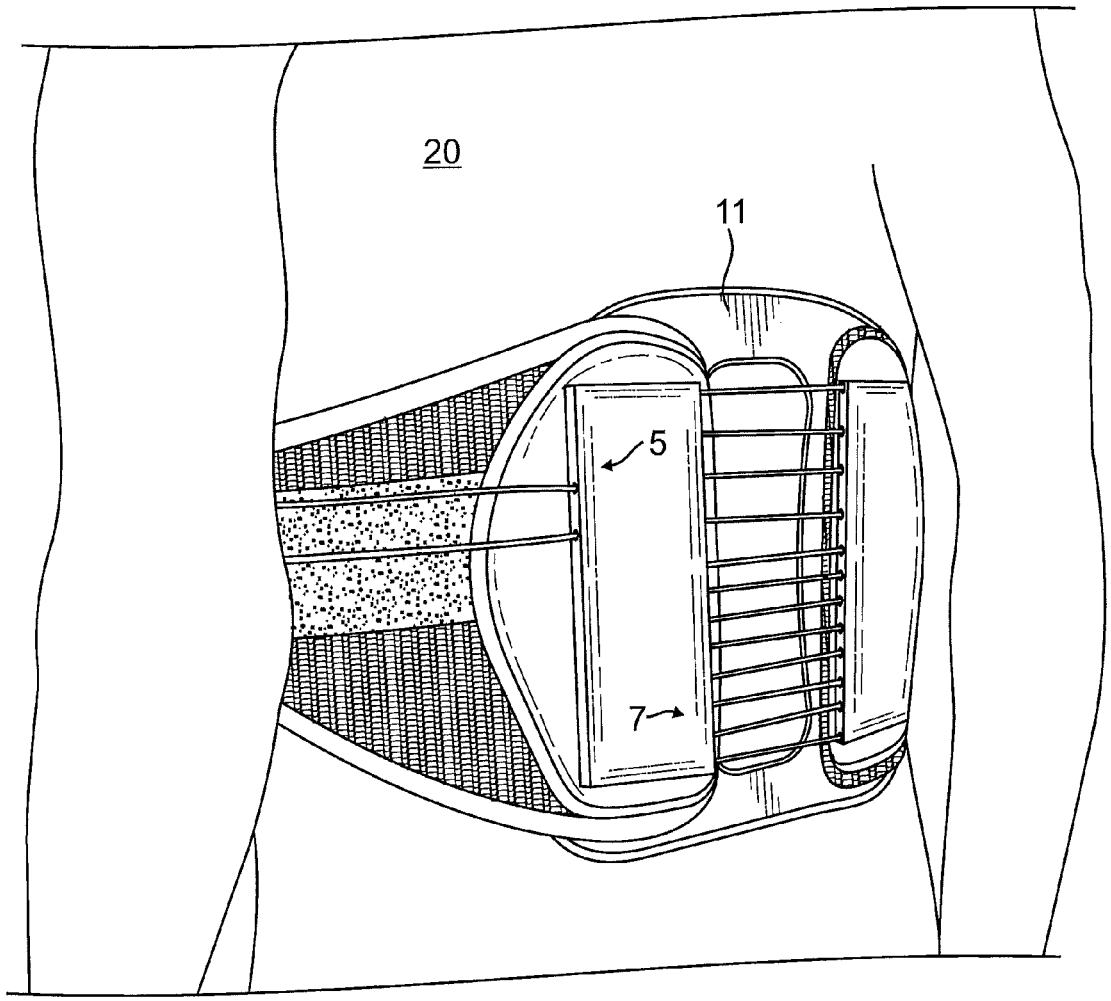
FIG. 3 shows another embodiment of a body panel having dynamic flex response in providing support to a posterior portion of the body removably attached to another body brace having a mechanical advantage for tightening the brace around the torso.
Figure 7:
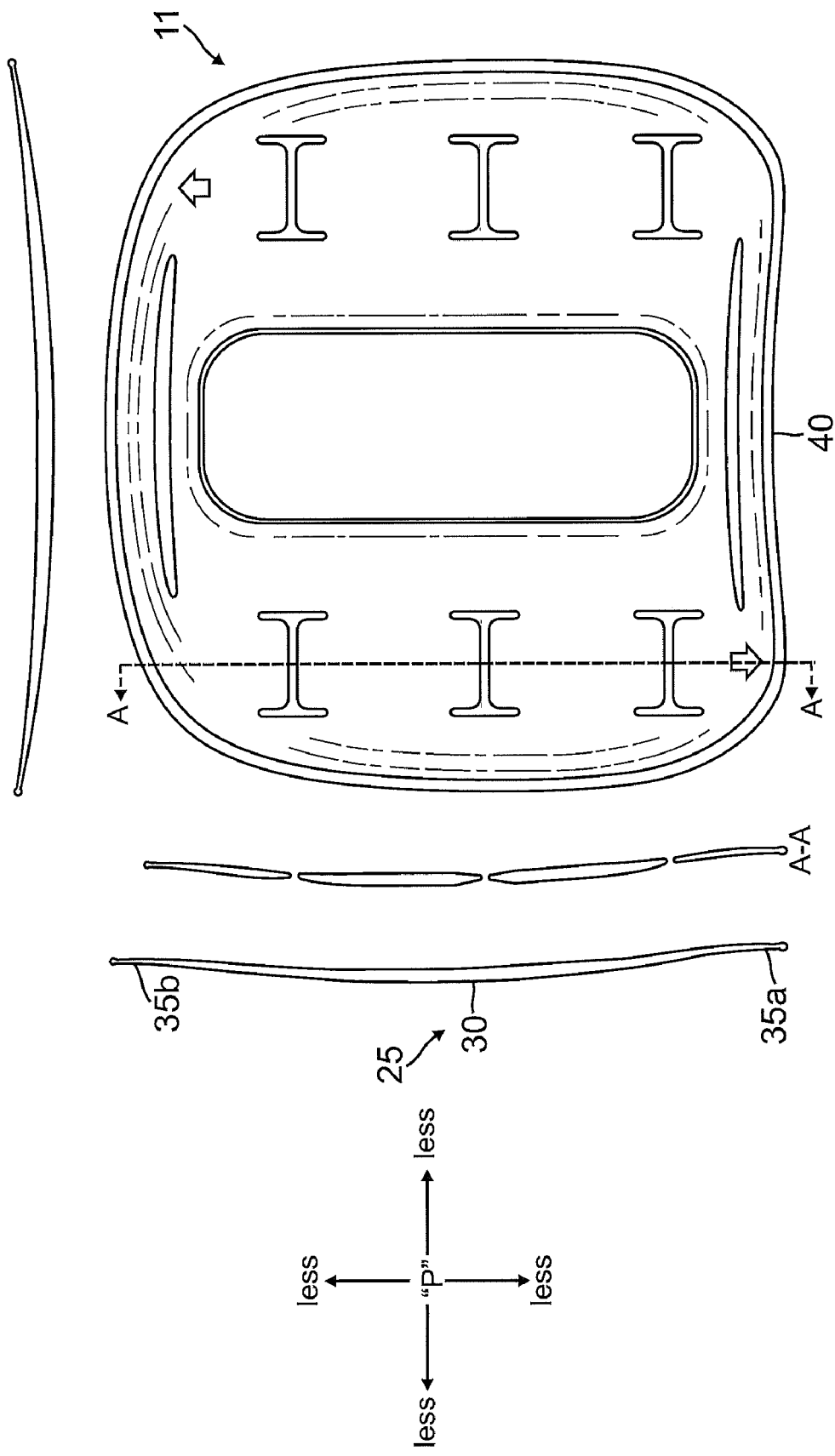
FIGS. 7-8 show a body panel having dynamic flex response in providing patient physiology contoured compression support to a posterior and/or anterior portion of the body.
Figure 8:
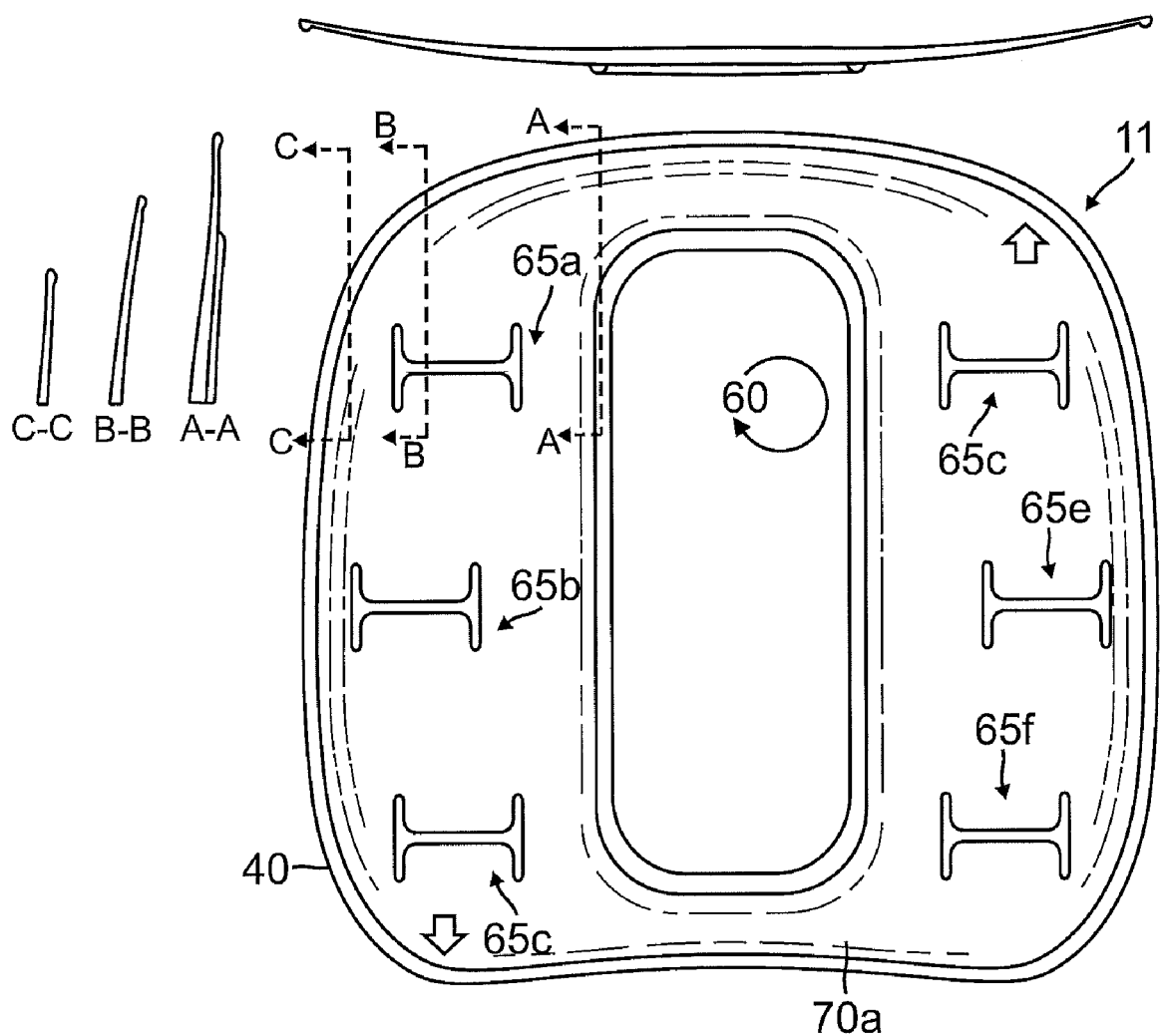
Figure 9:
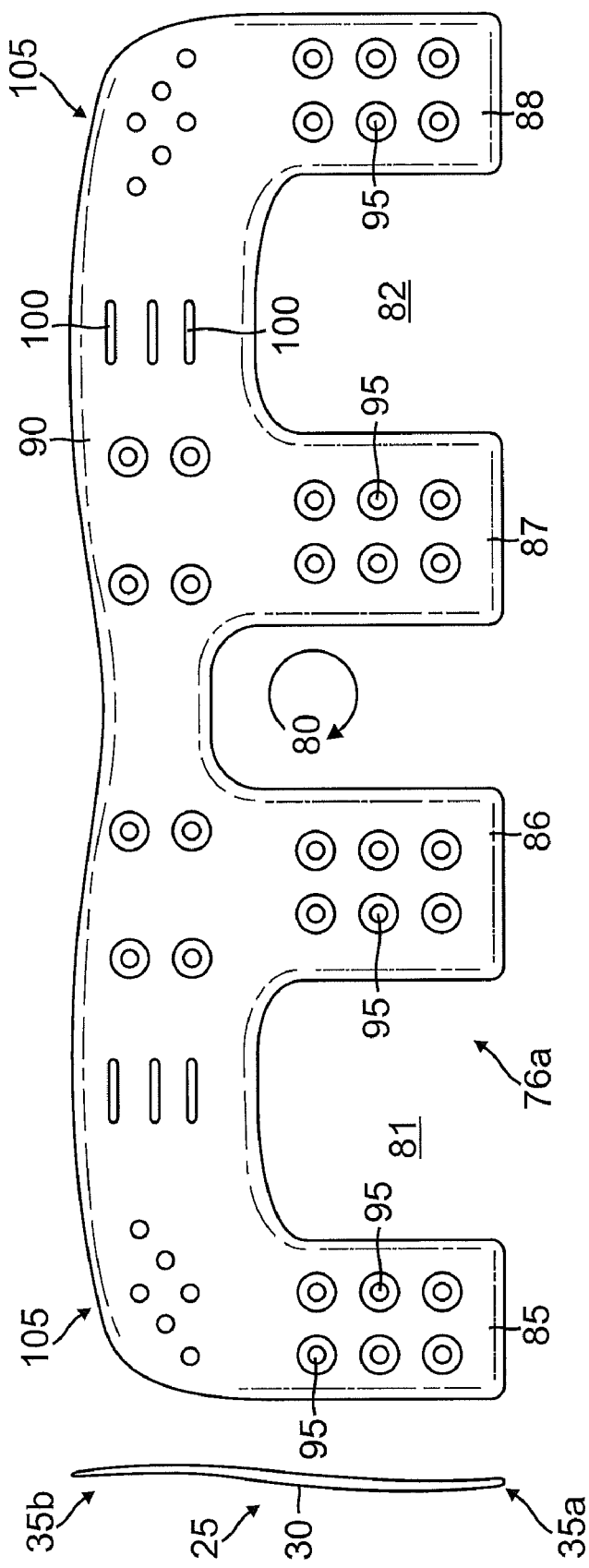
FIGS. 9-13 show a body panel configured to be assembled with another body panel having substantially the same size and shape to provide dynamic flex response while supporting a posterior portion of the body through a range of vertical height adjustments.
Figure 10:
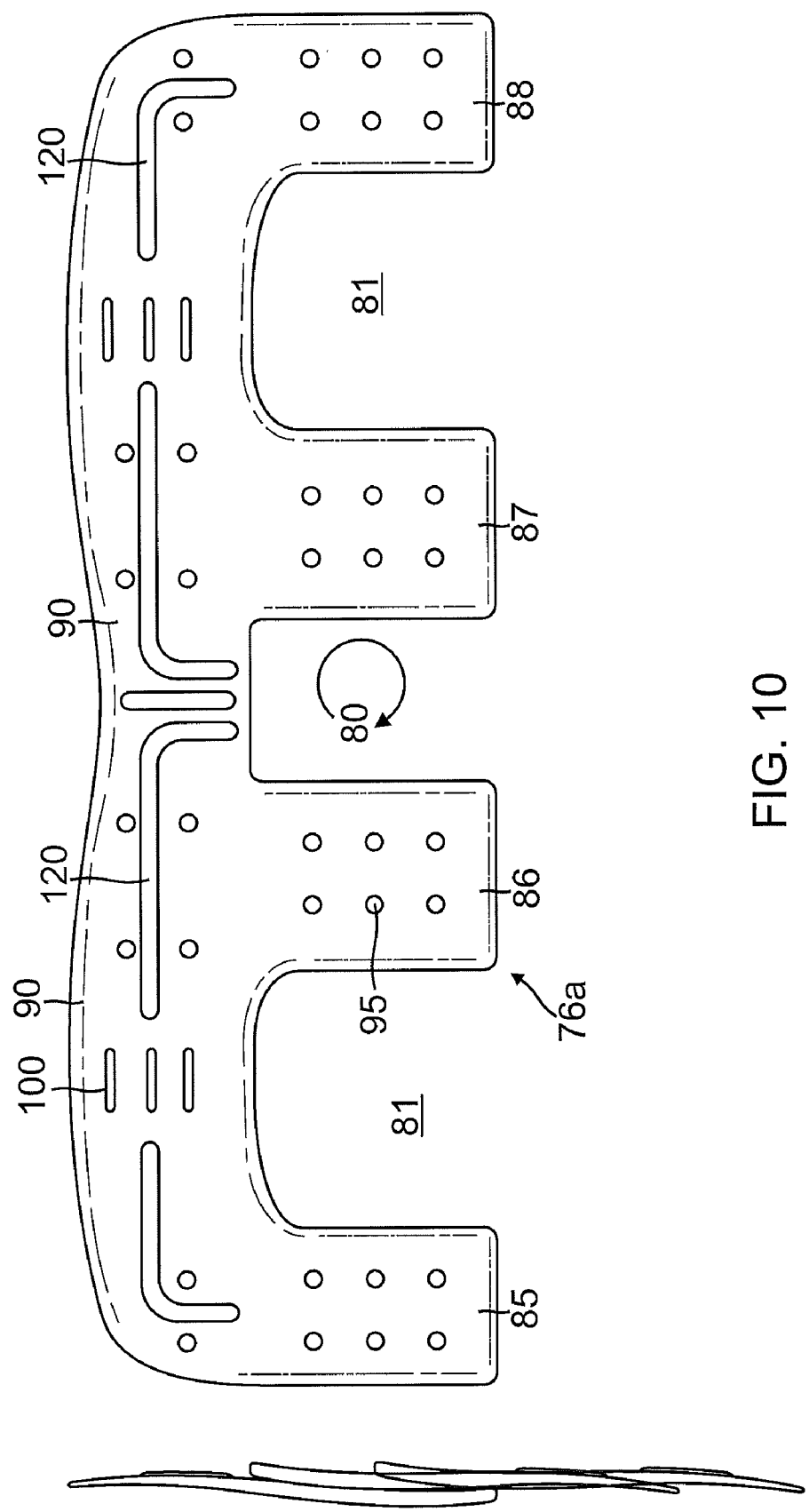
Figure 11:
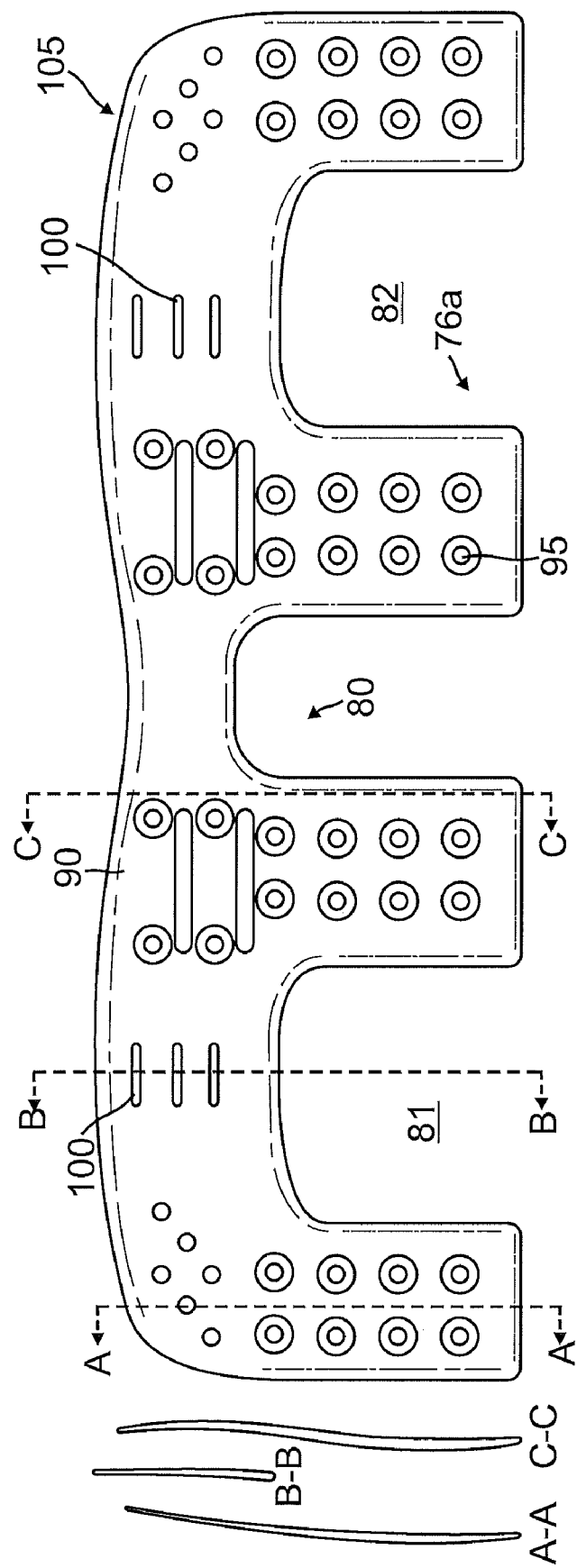
Figure 12:
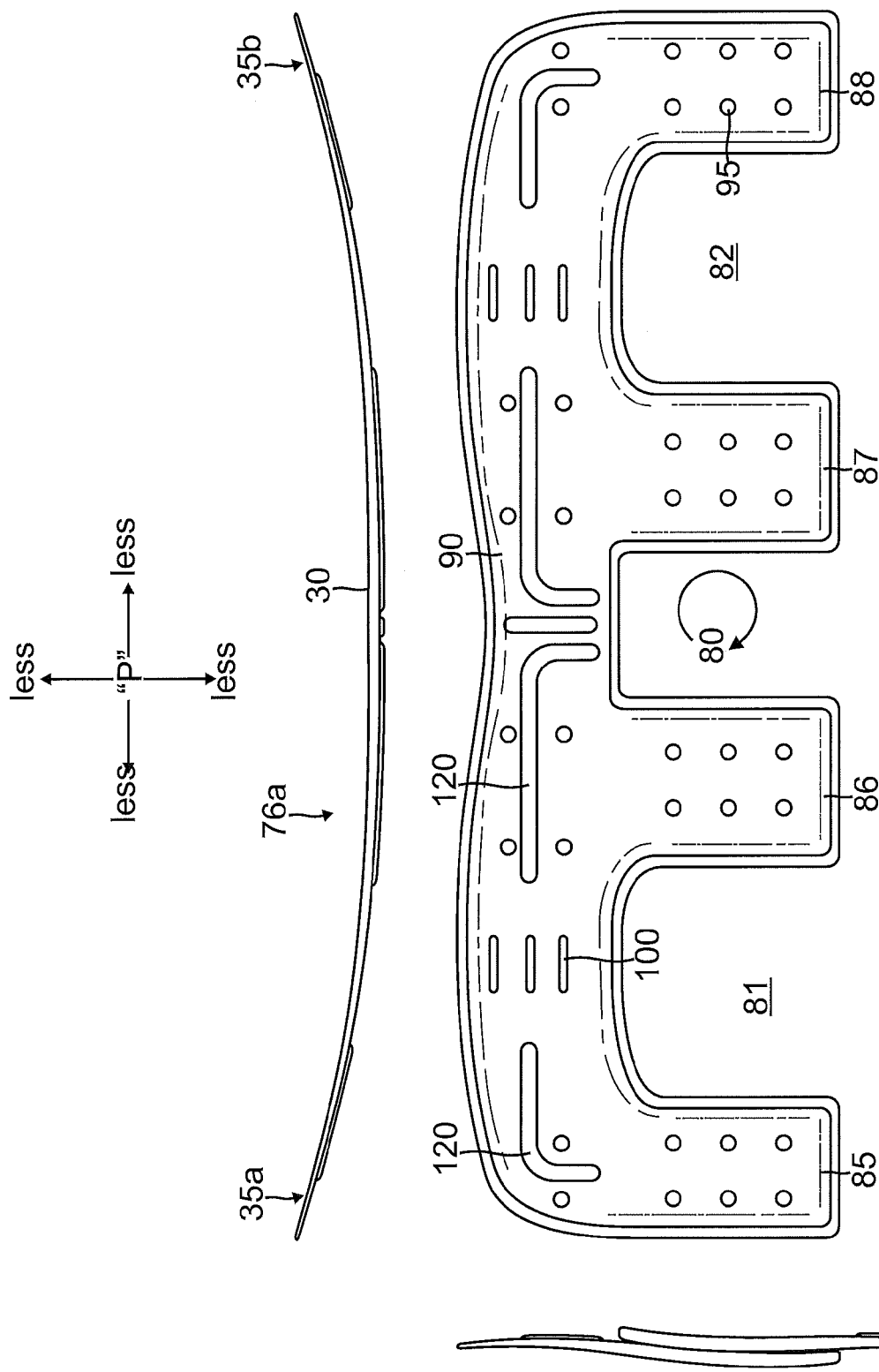

As shown in FIG. 3, and more particularly in FIG. 7 and FIG. 8, depending on various factors, including patient size and recommended treatment, in another embodiment, a relatively smaller sized posterior body panel 11 generally having all the features of the larger sized body panel 10 may be utilized to provide dynamic flex response when supporting a posterior body portion.

Similar to the larger size posterior body panel 10 shown at least in FIGS. 5 and 6, the smaller posterior body panel 11 shown in at least FIGS. 7 and 8, is positioned in an area of the lower back generally over the spinal cord and is shaped to provide support to the torso 20 from approximately the wearer's waist to about mid-back, and laterally to cover a majority of the wearer's lower back. As shown in FIG. 7, preferably, the posterior body panel 11 is contoured 25 to the physiology of the patient to contact a larger portion of the body to provide greater support and comfort than a similarly sized non-contoured panel. The body panel 11 is preferably lightweight and provides dynamic flex response when providing posterior body support. In this regard, the body panel 11 preferably includes a relatively stronger or more rigid core or inner 30 portion and relatively less rigid or more flexible portion at peripheral regions 35a, 35b.

As shown in the end view, top view, and cross-section A-A view of FIG. 7, the body panel 11 is relatively thicker near the center 30 and gets progressively thinner moving toward the periphery or edges 35a, 35b of the body panel 11. In this way the body panel 11 provides a progressive support system, indicated by reference "P", i.e., more support near the body's core or spine and relatively less support along the edges 35a, 35b where the body panel 11 is more forgiving to patient movement. Patient comfort may be further enhanced by a smooth bead along the perimeter of the body panel.

Other similarities to the body panel shown 10 in at least FIGS. 5 and 6 include a removed center section 60 and a plurality of cutouts or slots 65a-65f to facilitate removable attachment and vertical height adjustment of the posterior body panel 11 to the body brace 5.

Figure 4:
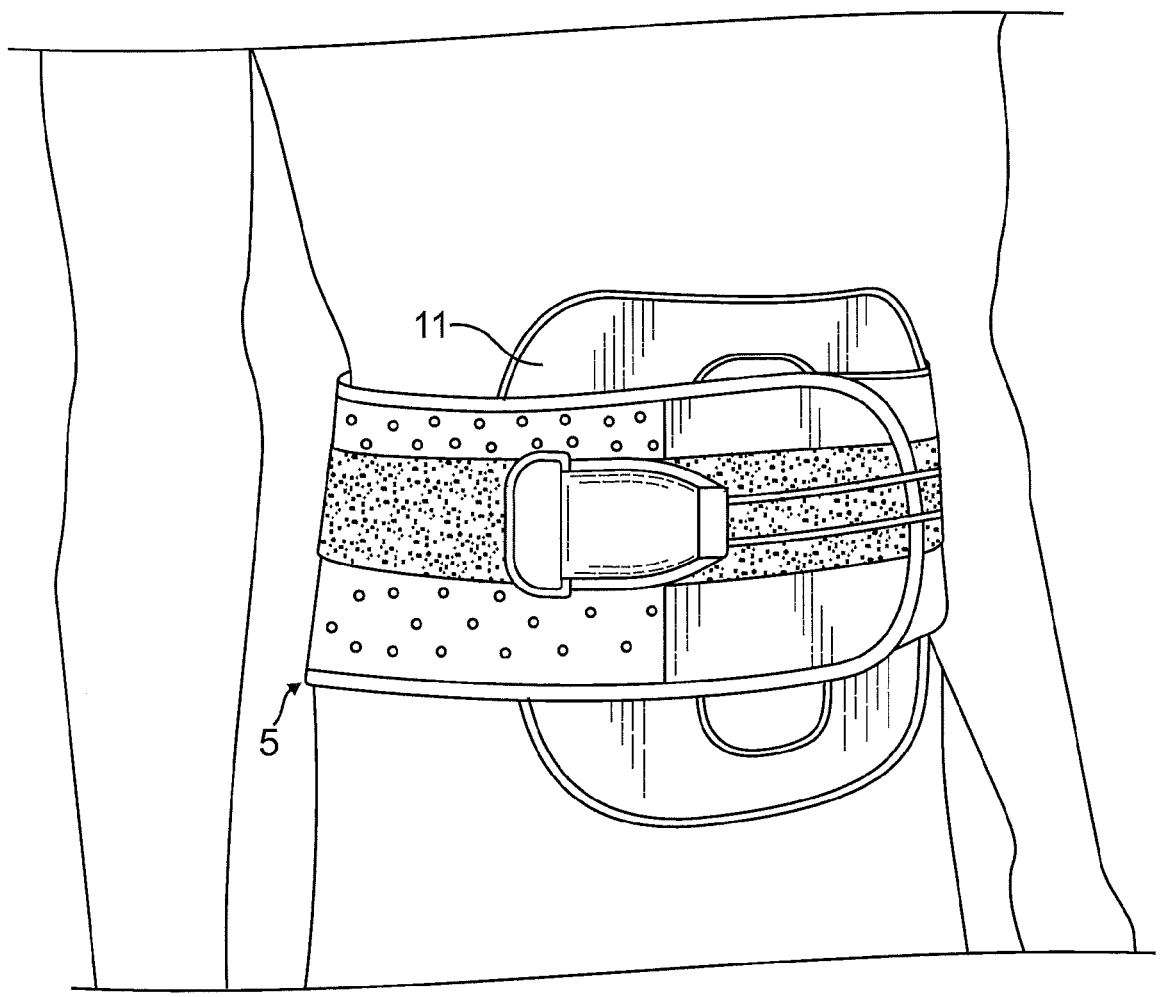
FIG. 4 shows the body panel of FIG. 3 providing support to an anterior portion of the body removably attached to a body brace having a mechanical advantage for tightening the brace around the torso of the body.

In contrast to the larger body panel 10 of FIGS. 5 and 6, the unique geometry of the relatively smaller body panel 11 allows it to be utilized as a posterior and/or an anterior body panel, see FIG. 4. In this regard, the body panel 11 is rotated 180° so that the bottom edge 70a (closer to the patient's waist) when worn as a posterior body panel 11 becomes the top edge (closer to the patient's upper back) when worn as an anterior body panel. As such, a single body panel 11 may be utilized as both an anterior and a posterior body panel to provide dynamic flex response when supporting the anterior and/or posterior body portions.

In another embodiment, the body brace 5 may include a body panel assembly 75 (FIG. 13) having top and bottom pieces 76a, 76b having substantially the same size and shape attached to each other, such as the body panel shown in FIGS. 9-15, to provide dynamic flex response when supporting a posterior and lateral portions of the body. Accordingly, the disclosure herein will focus on one body panel 76a of the body panel assembly 75 with the understanding that the body panel 76b of the body panel assembly 75, unless indicated otherwise, is substantially the same size and shape.

Similar to other body panels 10, 11 described herein, the body panels 76a, 76b shown in FIGS. 9-15 are preferably constructed of a relatively thin-walled polyethylene, polypropylene, or similar thermoformable ethylene materials. This feature permits the body panel 76a to wrap or curve substantially around the patient's body to create an inherently strong "cylinder" to support the patient's back, sides, and partial midsection, see the top view of FIG. 14 for example. When worn as prescribed, the body panel assembly 75 provides inherently strong circumferential compression, however, the body panels 76a, 76b are contoured 25 to the physiology of the patient to provide even greater support and comfort than a non-contoured panels. In addition, the body panels 76a, 76b are preferably lightweight and provide dynamic flex response when providing support to the body. In this regard, the body panels 76a, 76b preferably include a relatively stronger or more rigid core or inner portion 30 and relatively less rigid or more flexible support at peripheral regions 35a, 35b.

As primarily shown in the side views of FIGS. 9-15, the body panel 76a is relatively thicker near the center 30 and gets progressively thinner as near the periphery or edges 35a, 35b of the body panel 76. In this way the body panel 76a provides a progressive support system, indicated by reference "P" i.e., more support near the bodies core or spine and relatively less support along the edges 35a, 35b where the body panel 76a is more forgiving to patient movement.

The body panel 76a shown in FIG. 9-13 is sufficiently long enough to extend around the lateral or side portion of the body, to the front of the body from opposite sides of the spine. Accordingly, in one aspect, the body panel 76a provides circumferential support in a "chairback" like fashion to the patient's back, sides, and midsection. A center cutout 80 and lateral cutouts 81, 82 are preferably formed in the body panel 76a to provided open areas to facilitate incision maintenance or healing, or movement associated with the spine and hip regions of the body.

Figure 13:
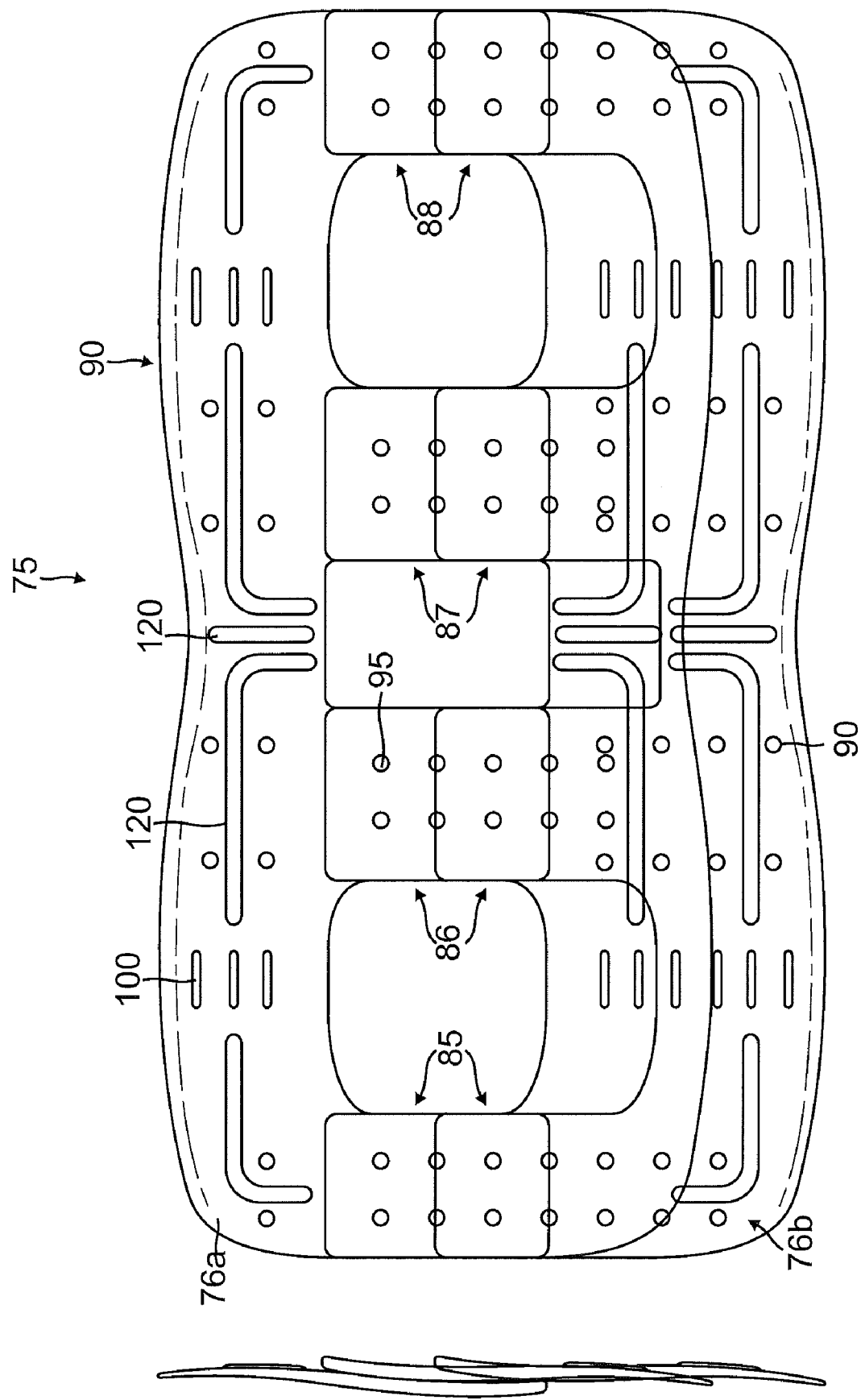

The body panel cutouts 80-82 are bordered on each side by connecting pieces 85-88 extending from an elongated main body panel portion 90 and parallel to each other. Each connection piece 85-88 includes a plurality of space apart orifices 95 structured to accept rivets (preferably constructed of plastic) that are preferably countersunk. In this regard, as shown in FIG. 13, aligning the orifices 95 of the top body panel 76a with the orifices 95 of the bottom body panel 76b permits vertical height adjustment of body panels 76a, 76b having substantially the same size and shape to be connected or assembled together while the rivet countersinks enhance user comfort by reducing or eliminating unnecessary protrusion, as well as making for an overall more finished product.

A plurality of slots 100 are preferably provided, appropriately space, and configured on the elongated main body panel portion 90 to accept straps for removably attaching the body panel(s) 76a, 76b to the body brace 5. Depending on the final vertical height (top to bottom) of the body panel assembly 75, the straps may be threaded through an upper slot to accommodate a relatively narrower body panel assembly 75 or threaded through a lower slot to accommodate a relatively wider body panel assembly 75.

Figure 16:
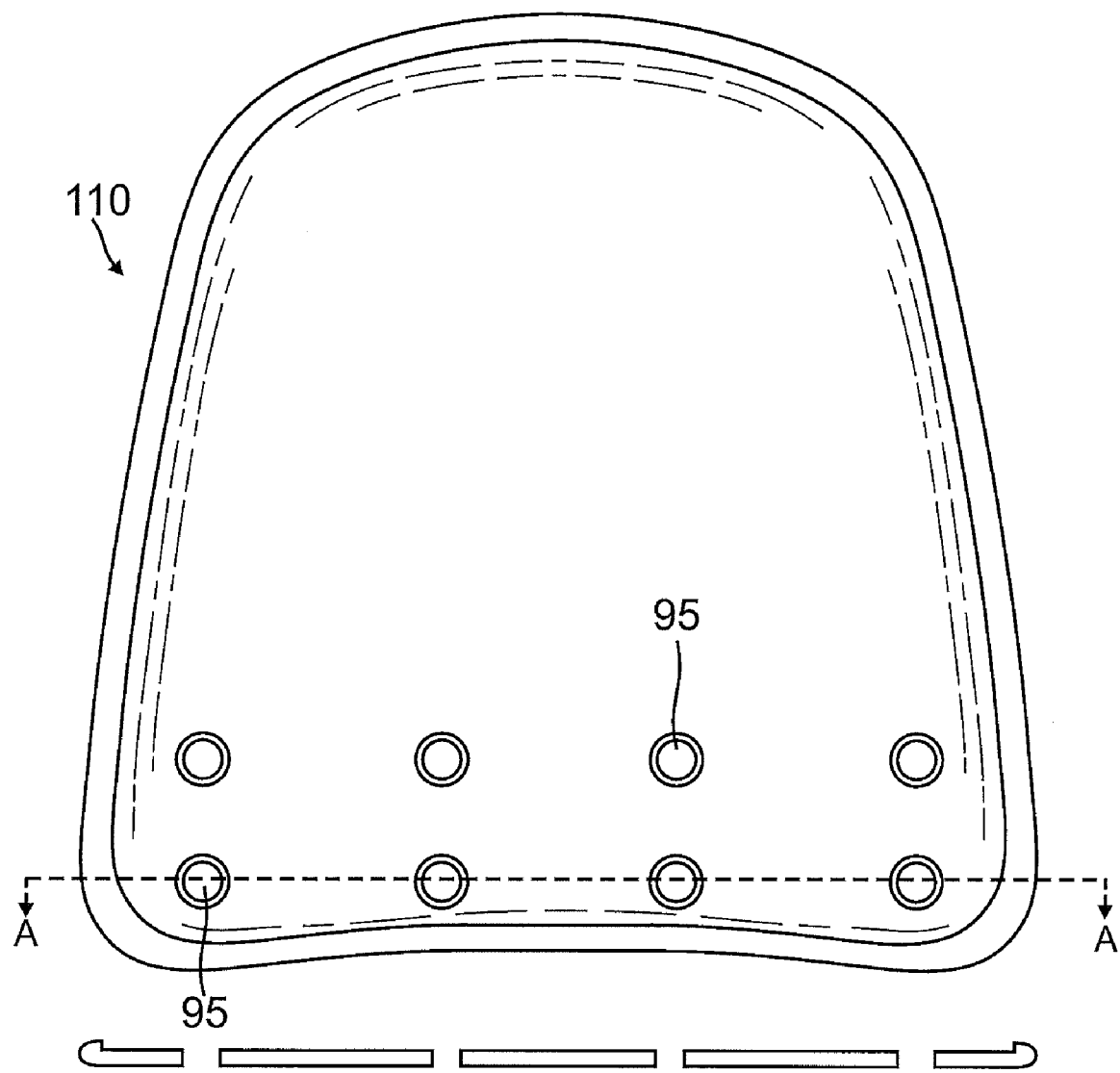
FIGS. 16-17 show exemplary embodiments of extension panels that may be associated or utilized with one embodiment of the body panel shown in FIGS. 9-13.
Figure 17:
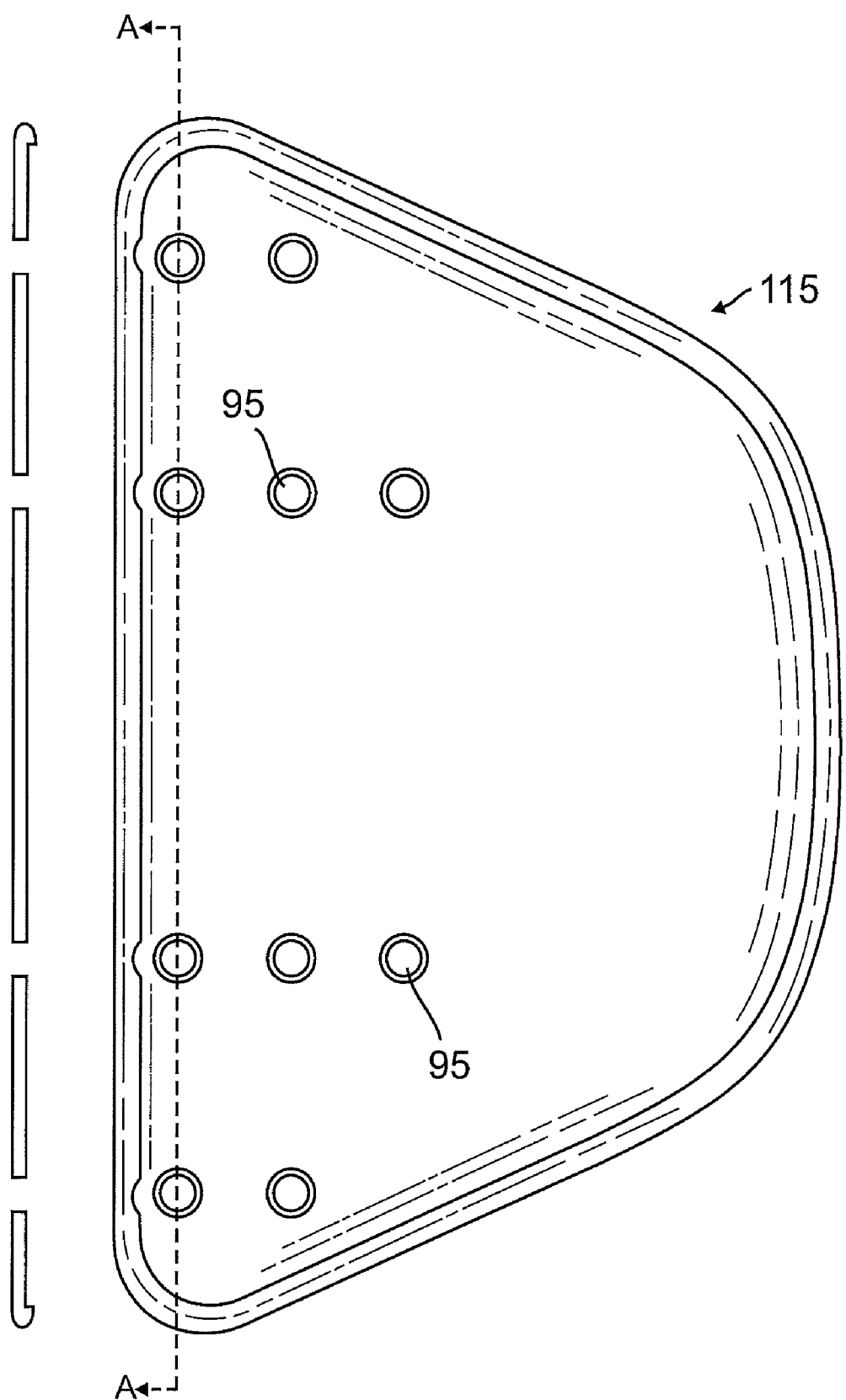

One or more attachment matrix(s) 105 comprising a plurality of holes and/or additional orifices 95 may be further provided on the elongated main body portion 90 for accepting a connecting rivet, bolt, screw, or similar item when attaching one or more corresponding extension panels 110, 115, such as those shown in FIGS. 16 and 17. The extension panels 110, 115 including orifices 95 for mating with the orifices 95 located on the elongated main body portion 90 and further include dynamic flex response in providing support to the body.

The body panel 76a may further include ribs 120 horizontally, vertically, and/or a combination thereof positioned at least along the elongated main body portion 90 to provide structural strength to the body panel 76a.

As shown in FIG. 13, in one embodiment, body panels 76a, 76b having substantially the same size and shape are positioned to have one panel 76a form a top portion and the other body panel 76b form a bottom portion of a body panel assembly 75. In this regard, the panels 76a, 76b are position to have their elongated main body portions 90 opposite each other, one forming a top support and the other forming a bottom support, with their respective connecting pieces 85-88 extending therebetween to overlap with each other so that corresponding orifices 95 of the connecting pieces 85-88 are aligned with each other. By aligning the orifices 95 appropriately, the top to bottom distance (vertical height) of the body panel assembly 75 is adjusted and the body panels 76a, 76b are assembled using plastic rivets or similar connecting means into a body panel assembly 75. The body panel assembly 75 is then attached to the body brace 5 by straps threaded through the appropriate slots 100. The body brace 5 is then positioned on the patient and wrapped around the person's torso 20. Velcro closures may be used to provide a first level of body brace support to the torso 20, however, preferably, a secondary body brace support, such as a pulley system 7 that provides a mechanical advantage so as to require a minimal effort on the part of the patient when tightening the orthotic around the torso 20 is further provided to secure the body brace 5 and provide support to the torso 20.

Figure 14:
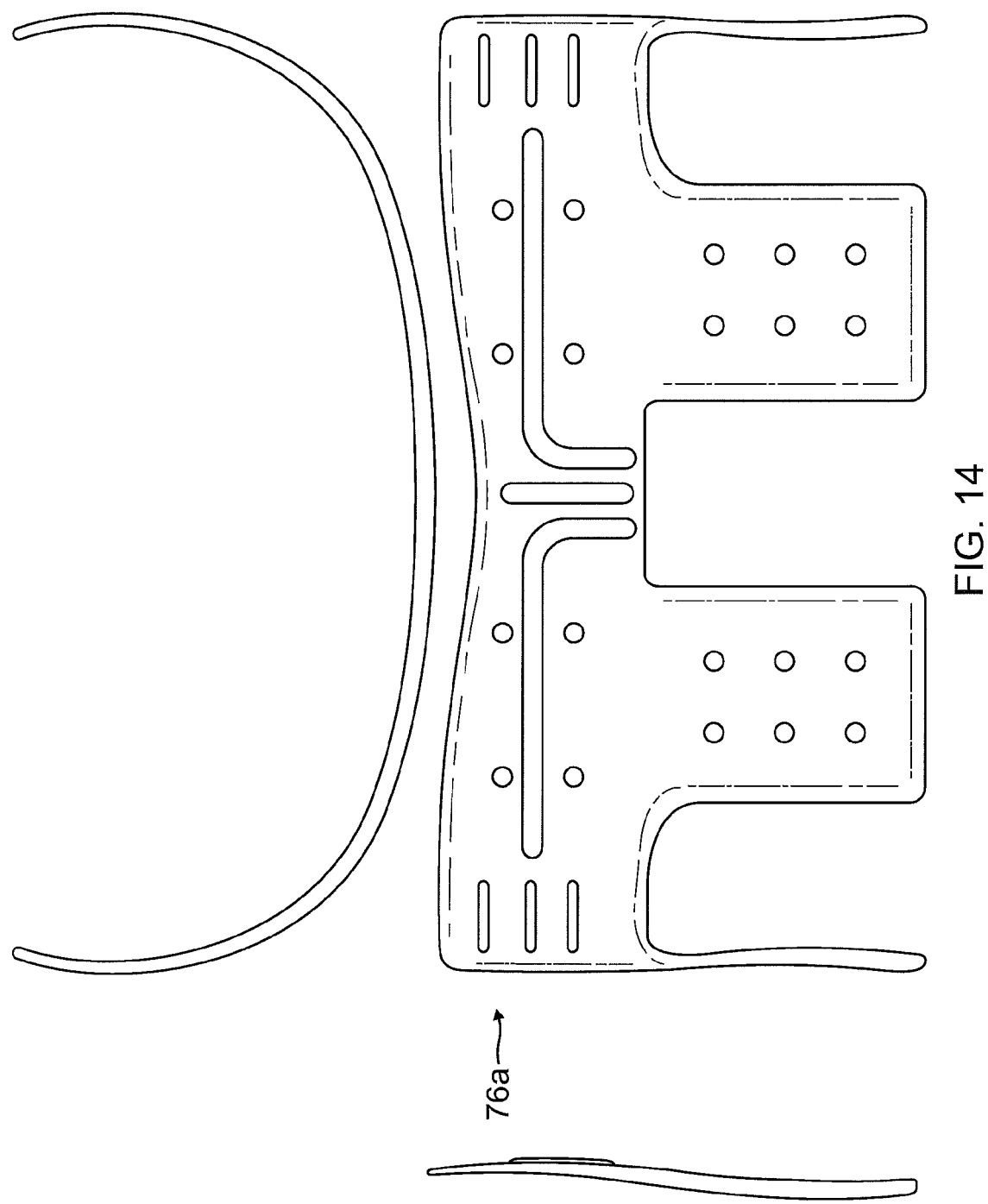
FIGS. 14-15 show another embodiment of body panel configured to be assembled with another body panel having substantially the same size and shape, each panel having dynamic flex response in providing patient physiology contoured compression support to a posterior portion of the body.
Figure 15:
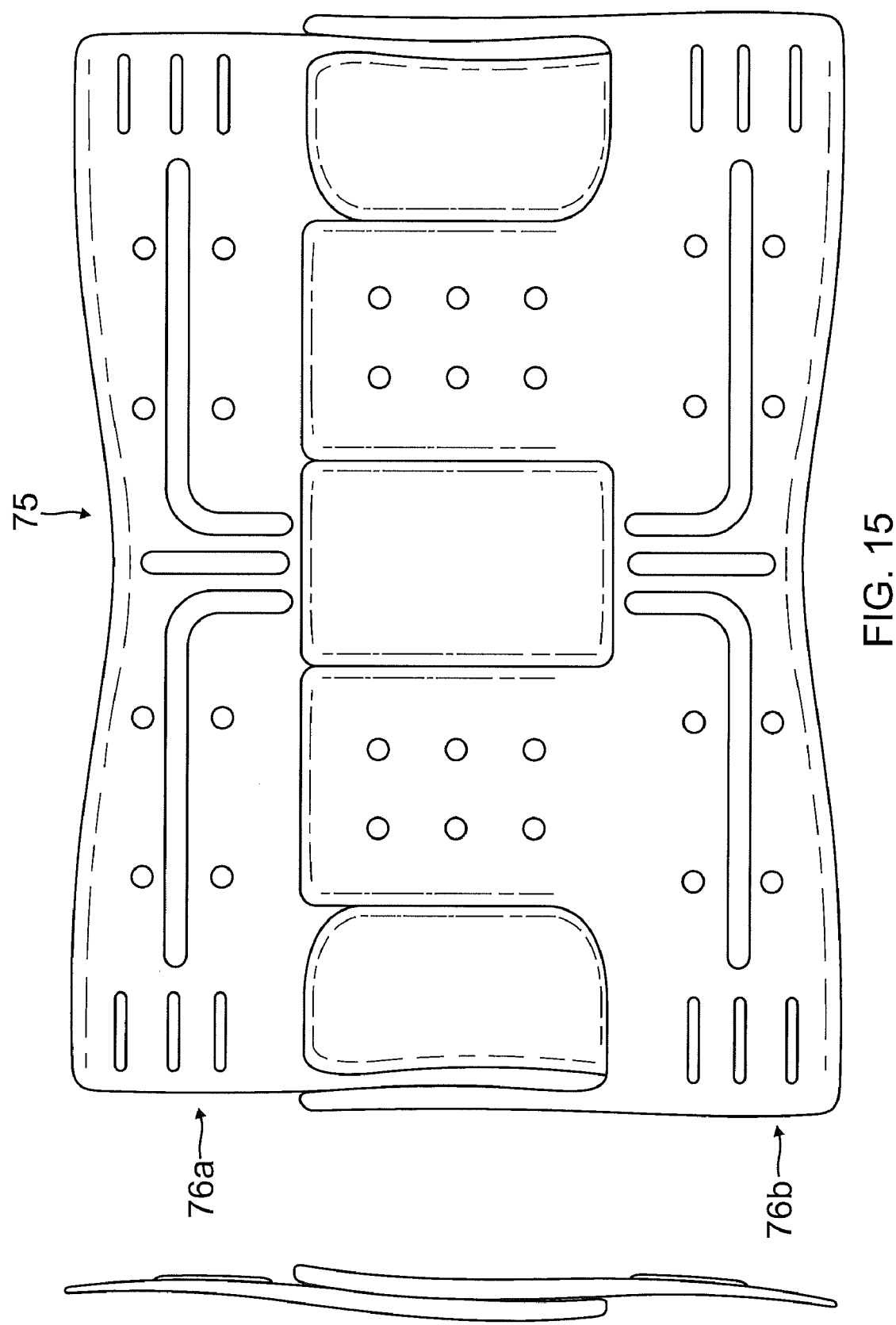

As shown in FIG. 14 and FIG. 15, as long as the body panels 76a, 76b are substantially the same size and shape, the body panels 76a, 76b may be sized and assembled into a body brace assembly 75 to accommodate different individual physiologies.

In summary, a modular type body brace 5 is described herein. The body brace 5 preferably includes one or more interchangeable removably attached lightweight posterior and/or anterior body panels 10, 11, that may be capable of vertical height adjustment, and shaped and contoured 25 to the physiology of the patient. Each body panel 10, 11 preferably provides progressive dynamic flex response when supporting anterior and/or posterior body portions to ensure patient comfort and support. In one embodiment, body panels including an anterior 11 panel, a "chairback" frame 75, and a posterior panel 10, 11 for providing rigidity, support, and comfort in a lightweight, ventilated construction for greater patient compliance.

The apparatus and methods of the present invention have been described with some particularity, but the specific designs, constructions and steps disclosed are not to be taken as delimiting of the invention. Obvious modifications will make themselves apparent to those of ordinary skill in the art, all of which will not depart from the essence of the invention and all such changes and modifications are intended to be encompassed within the appended claims.

What is claimed:

1. An orthotic device, comprising:
a body brace worn about a portion of the body; and
one or more removably attached body panels associated with the body brace for supporting the portion of the body, wherein the body panels are contoured to the physiology of the portion of the body and have a relatively thicker core and progressively thinner peripheral region so as to provide dynamic flex response in response to forces applied to the brace or one or more body panels when supporting the portion of the body.

2. An orthotic device, comprising:
a body brace worn upon the body; and
a removably attached body panel associated with the body brace for supporting a portion of the body, wherein the body panel is contoured to the physiology of the body portion and has a progressive support structure that includes a relatively thicker core and progressively thinner peripheral region so as to provide dynamic flex response in response to forces applied to the body panel when supporting the body portion.

3. The orthotic device of claim 2, wherein the progressive support structure progresses horizontally along an upper or a lower section of the body panel.

4. The orthotic device of claim 2, wherein the progressive support structure progresses vertically along a right lateral portion or a left lateral portion of the body panel.

5. The orthotic device of claim 2, wherein the progressive support structure progresses horizontally along an upper or a lower section of the body panel, and vertically along a right lateral portion or a left lateral portion of the body panel.

6. The orthotic device of claim 2, wherein the body panel is associated with the body brace to support an anterior body portion.

7. The orthotic device of claim 2, wherein the body panel is associated with the body brace to support a posterior body portion.

8. The orthotic device of claim 7, wherein the body panel is associated with the body brace to support a portion of the lower back generally over the spinal cord and is shaped to provide support to at least minimize the spine from being hyperextended.

9. The orthotic device of claim 2, wherein the body panel includes a central cutout to facilitate access to an incision site of the body.

10. The orthotic device of claim 2, wherein the body panel further includes a plurality of cutouts or slots to facilitate removable association and vertical height adjustment of the body panel to the body brace.

11. The orthotic device of claim 10, wherein the cutouts or slots are shaped to threadingly accept a connecting strap therethrough to removably associate the body panel to the body brace.

12. The orthotic device of claim 2, wherein the body panel further includes an upper right relief portion and an upper left relief portion shaped along respective right and left upper lateral portions of the body panel to allow generally unrestricted movement of the scapulas.

13. The orthotic device of claim 2, wherein the body panel is associated with the body brace and configured to support a posterior body portion or a lateral body portion.

14. An orthotic device, comprising:
a body brace worn upon the body; and
an attached body panel associated with the body brace, the body panel including an elongated flexible top piece and an identically shaped elongated flexible bottom piece, the top piece and the bottom piece are attached to each other and configured to support the body along the back, sides, and partial midsection;
wherein the body panel is contoured to the physiology of the body and has a progressive support structure that includes a relatively thicker core and progressively thinner peripheral region so as to provide dynamic flex response in response to forces applied to the body panel when supporting the body.

15. The orthotic device of claim 14, wherein the progressive support structure progresses horizontally along an upper or a lower section of the body panel.

16. The orthotic device of claim 14, wherein the progressive support structure progresses vertically along a right lateral portion or a left lateral portion of the body panel.

17. The orthotic device of claim 14, wherein the progressive support structure progresses horizontally along an upper or a lower section of the body panel, and vertically along a right lateral portion or a left lateral portion of the body panel.

18. The orthotic device of claim 14, wherein the top piece and the bottom piece each includes an elongated main body panel portion having a plurality of periodically spaced support sections extending therefrom for supporting the body and for removable connection of the top piece to the bottom piece.

19. The orthotic device of claim 18, wherein each of the support sections of the top piece and the bottom piece includes a plurality of spaced apart orifices structured to accept a connecting member to permit vertical height adjustment of the top piece and the bottom piece relative to each other.

20. An orthotic device, comprising:
a body brace worn upon the body; and
an attached body panel associated with the body brace, the body panel including an elongated flexible top piece and an identically shaped elongated flexible bottom piece, the top piece and the bottom piece are attached to each other and configured to support the body along the back, sides, and partial midsection;
wherein the top piece and the bottom piece each includes an elongated main body panel portion having a plurality of periodically spaced support sections extending therefrom for supporting the body and for removable connection of the top piece to the bottom piece.

21. The orthotic device of claim 20, wherein the body panel is contoured to the physiology of the body and has a progressive support structure that includes a relatively thicker core and progressively thinner peripheral region so as to provide dynamic flex response in response to forces applied to the body panel when supporting the body.

22. The orthotic device of claim 21, wherein the progressive support structure progresses horizontally along an upper or a lower section of the body panel.

23. The orthotic device of claim 21, wherein the progressive support structure progresses vertically along a right lateral portion or a left lateral portion of the body panel.

24. The orthotic device of claim 21, wherein the progressive support structure progresses horizontally along an upper or a lower section of the body panel, and vertically along a right lateral portion or a left lateral portion of the body panel.

25. The orthotic device of claim 20, wherein each of the support sections of the top piece and the bottom piece includes a plurality of spaced apart orifices structured to accept a connecting member to permit vertical height adjustment of the top piece and the bottom piece relative to each other.

* * * * *